United States Patent [19]

Powell et al.

[11] Patent Number: 5,008,470

[45] Date of Patent: Apr. 16, 1991

[54] PROCESS FOR PREPARING A BISPHENOL

[75] Inventors: Joseph B. Powell; Christopher W. Uzelmeier, both of Houston, Tex.

[73] Assignee: Shell Oil Company, Houston, Tex.

[21] Appl. No.: 444,580

[22] Filed: Nov. 30, 1989

[51] Int. Cl.$^5$ .............. C07C 37/20; C07C 39/16
[52] U.S. Cl. .................... 568/727; 568/724; 568/728
[58] Field of Search ............... 568/722, 724, 727, 728

[56] References Cited

U.S. PATENT DOCUMENTS

| | | | |
|---|---|---|---|
| 4,160,110 | 7/1979 | Carnahan, Jr. | 568/703 |
| 4,169,211 | 9/1979 | Ligorati et al. | 568/724 |
| 4,396,728 | 8/1983 | Faler | 521/32 |
| 4,533,764 | 8/1985 | Chang et al. | 568/724 |
| 4,766,254 | 8/1988 | Faler et al. | 568/724 |
| 4,876,395 | 10/1989 | Kissinger | 568/728 |

FOREIGN PATENT DOCUMENTS 5821633  7/1981  Japan .................. 568/727
58021633 2/1983  Japan .

*Primary Examiner*—Werren B. Lone

[57] ABSTRACT

The present disclosure is directed to acid scavenging in the acid-catalyzed preparation of a bisphenol by condensation of a phenolic compound and a carbonyl compound. During the preparation, strong acids leach from the acidic ion exchange resin catalyst into the reaction effluent. These acids can be scavenged effectively and without contamination by an inorganic oxide before purification of the product. The acid scavenging improves the product quality and yield by reducing acid catalyzed cracking of bisphenols during purification and finishing steps.

13 Claims, 3 Drawing Sheets

PROCESS FOR PREPARING A BISPHENOL

BACKGROUND OF THE INVENTION

This invention relates to the preparation of a bisphenol. In one aspect, the invention relates to improving purity and yield in a process to manufacture a bisphenol employing an acidic ion exchange resin catalyst.

Bisphenols are used as the starting material in the manufacture of resins such as polycarbonate resins and epoxy resins. It is important that the bisphenol starting material is as pure as possible in order to avoid adverse effects on the properties of resulting resins.

Bisphenols can be manufactured over a strong acid ion exchange resin catalyst by condensation of a phenol and a ketone or an aldehyde. During the preparation process, it has been found that strong acids leach from the acid catalyst into the reaction effluent. This soluble acidity catalyzes cracking of the bisphenol during subsequent purification and finishing steps which results in lower product purity and a decrease in product yield.

If a sulfonated organic polymer is used as the acidic ion exchange resin catalyst, strong organic acids such as phenol sulfonic acid have been found to leach into the reaction product mixture. As an example, typically for bisphenol-A (BPA), the product stream from the reaction zone containing BPA in solution is passed to a crystallization zone, wherein the BPA is crystallized as an adduct with phenol and the remaining solution, or "mother liquor," is recycled to the reaction zone. The leached acid will remain in the separated product stream with the crystallized BPA and cause degradation of the BPA product during subsequent process steps, particularly if thermal finishing steps are involved. It has been found that the soluble acid leached from the acidic ion exchange resin acts as a catalyst for cracking of BPA during the thermal finishing step, which results in a lower product purity and a decrease in product yield.

In order to obtain bisphenols with higher purity, it is known to use an amine-based organic anion exchange resin to remove acidic impurities from the mother liquor. Such amine-based resins are expensive and inherently less stable than the catalyst resin, and their use can result in the presence of soluble amines or the reaction products of these amines with phenol in the product stream, which will decrease product quality. When the amine-based resin is used in a recycled system, the soluble amines will in turn poison the acidic ion exchange catalyst upon recycle of unconverted reactant. Such amine-based organic resins are typically regenerated by aqueous base, which is also a poison for the acidic ion exchange resin catalyst.

It is therefore an object of the present invention to provide an acid ion exchange resin catalyzed bisphenol preparation process with improved purity and yield. It is another object of the present invention to provide a process to remove acidic impurities from a recycled system without poisoning the acid ion exchange resin catalyst.

SUMMARY OF THE INVENTION

According to the invention, a process for the production of a bisphenol is provided, the process comprising the steps of:

(A) reacting a carbonyl compound with a stoichiometric excess of a phenolic compound in the presence of an effective amount of an acid ion exchange resin catalyst to produce a reaction product mixture comprising a bisphenol;

(B) contacting the reaction product mixture with an inorganic oxide adsorbent under conditions effective to reduce the acidity of the reaction product mixture; and (C) recovering bisphenol from the thus treated reaction product mixture.

DETAILED DESCRIPTION OF THE INVENTION

According to the invention, a high purity bisphenol can be produced in high yield by contacting a reaction product mixture containing a bisphenol with an inorganic oxide adsorbent. The reaction product mixture is the effluent of a reaction zone wherein a carbonyl compound and a phenolic compound are allowed to react in the presence of an effective amount of an acid ion exchange resin catalyst.

The phenolic compounds employed as the starting material in the production of bisphenols according to the invention are any compounds containing an hydroxy group linked to a carbon of an aromatic group. Suitable phenolic compounds include, for example, phenols and substituted phenols, such as: phenol, cresols, xylenols, chlorophenols, thymol, carvacrol, cumenol, 2-methyl-6-ethylphenol, 2,4-dimethyl-3-ethylphenol, 4-ethylphenol, 2-ethyl4-methylphenol, 2,3,6-trimethylphenol, 2-methyl-4-tertiary-butylphenol, 2,4-ditertiary-butyl-phenol, 4-methyl-2-tertiary-butylphenol, 2-tertiary-butyl-4-methylphenol, 2,3,5,6-tetramethylphenols, 2,6-dimethyl-phenol, 2,6-ditertiary-butylphenol, 3,5-dimethylphenol, 3,5-diethylphenol, 2-methyl-3,5-diethylphenol, o-phenylphenol, p-phenylphenol, the naphthols, phenanthrol, their homologues and analogues. Suitable phenolic compounds include those containing one or more phenolic group in each nucleus as well as polynuclear compounds.

The carbonyl compounds employed as the starting material can be any compound of the following formula:

wherein $R_1$ represents a member of the group consisting of any aliphatic, cycloaliphatic, aromatic and heterocyclic radicals, and $R_2$ represents a member of the group consisting of hydrogen, aliphatic, cycloaliphatic, aromatic and heterocyclic radicals. Suitable carbonyl compounds include ketones and aldehydes. Examples of suitable ketones include, for example, acetone, 1,3-dichloroacetone, dimethyl ketone, methyl ethyl ketone, diethyl ketone, dibutyl ketone, methyl isobutyl ketone, cyclohexanone, propionylphenone, methyl amyl ketone, mesityl oxide, cyclopentanone, acetophenone, and examples of suitable aldehydes include acetaldehyde, propionaldehyde, butyraldehyde and benzaldehyde.

The specific phenolic compound and carbonyl compound employed as starting material will depend upon the specific bisphenol compound desired and may be governed to some extent by specific operating conditions employed. The invention process is particularly suitable for production of bisphenol-A, for which the carbonyl compound is acetone and the phenolic compound is phenol. Typically, excess phenol is used for the condensation reaction. Preferably the ratio of phenol to carbonyl compound is within the range of about 20:1 to 2:1, generally about 12:1 to 2:1.

Acidic ion exchange resins usable in the condensation reaction of phenolic compound and carbonyl compound according to the present invention include essentially all known acidic ion exchange resins. Sulfonated resins are generally preferred. In particular, a sulfonated aromatic organic polymer as the ion exchange resin catalyst is quite suitable.

Various acidic ion exchange resins are disclosed, for example, in U.S. Pat. Nos. 2,597,438, 2,642,417, 3,172,916, 3,394,089, 3,634,341, 4,045,379, 4,396,728 and 4,455,409. Some examples of suitable commercially available sulfonated resins are: M-31 and G-26 manufactured by Dow Chemical Company; A-15, A-31, XE-561, XE-383 and XE-386 manufactured by Rohm and Haas; and SC-102 and SC-104 manufactured by Bayer-Lewatit.

The reaction is preferably executed in the presence of an added promoter for the acid-catalyzed reaction. Any known promoters for the acid catalyzed condensation of a phenolic compound and a carbonyl compound are suitable. Suitable promoters are mercaptan groups which are either free or bound to a resin. An alkyl mercaptan and bis-mercapto ethanolamine are examples of suitable promoters for the invention process.

In order to obtain bisphenols with improved yields and higher purities according to the invention process, the effluent of the reaction zone is contacted with an inorganic oxide adsorbent under conditions effective to reduce the acidity of the effluent. A portion of the excess phenol is optionally removed by flashing prior or after the acid removal step. The preferred inorganic oxide adsorbents are any amphoteric oxide substrates, which are oxides that have the capacity to behave either as an acid or a base. The preferred amphoteric oxide substrate has an isoelectric point above the pH of the effluent, such that the oxide will act as a weak-base anion exchanger. Examples of suitable oxides which can be employed are alumina, zirconium oxide, titanium oxide and tin oxide. In particular, use of activated alumina is preferred because of its ready availability and demonstrated effectiveness.

The effluent is preferably contacted with a fixed-bed inorganic oxide adsorbent in either an upflow or downflow configuration, wherein the weight hourly space velocity (WHSV) is within the range of about 0.2 to 10, preferably about 0.5 to 3. The WHSV in the acid scavenging zone may vary considerably within the scope of the invention depending to some extent upon the specific bisphenol products, the catalyst, the acid loss rate from the reaction and the adsorbent used, but is preferably within the range of about 0.2 to 10 in order to obtain acid concentrations of less than about 0.1 ppm in the effluent after treatment. The inorganic oxide adsorbent can be in any shape or form. The particle size is preferably within the range of about 0.4 to 1.2 mm diameter, and the surface area is preferably greater than about 50 $m^2/g$. The pore sizes typically range from about 50 to 500 angstroms.

For convenience, the invention process will be specifically described in terms of its most preferred embodiment, in which acetone and an excess of phenol are contacted in a reaction zone in the presence of a sulfonated cationic exchange resin catalyst and free mercaptan to produce BPA. The reaction is carried out in one or a series of reactors operated at temperatures within the range of about 60 to about 90° C. The reaction effluent includes bisphenol-A, acetone, water, mercaptan, phenol, various phenolic by-products of the reaction, and acids leached from the catalyst. After removing a portion of excess phenol by flashing, the effluent is passed through a fixed bed inorganic adsorbent to remove acid at temperatures within the range of about 65 to about 130° C. In an optional embodiment of the invention process, the acid removal step can be carried out prior to the flashing step.

Subsequently, BPA can be purified and removed from the adsorbent-treated effluent by various methods. Suitable means for recovering bisphenols include one or more of such steps as, distillation, solvent extraction, stratification, extractive distillation, adsorption, crystallization, filtration, centrifugation and thermal liberation. Typically, the BPA is isolated by passing the treated reaction product stream containing BPA to a crystallization zone, where the stream is cooled to crystallize a BPA-phenol adduct or treated with water to crystallize the BPA. Slurries of crystallized BPA or crystalline adducts of BPA are from the remaining solution by filtration or by centrifugation and the remaining filtrate or "mother liquor" is recycled to the reaction zone. In a finishing zone, BPA isolated as a crystalline adduct is converted to BPA by thermally stripping phenol from the adduct and recrystallizing, and the water-crystallized BPA is dried. More than one such step can be employed in the finishing zone to purify BPA. Subsequently, the purified BPA is recovered. Similar process can be used to recover other bisphenols.

In an optional embodiment of the invention process, the acid removal step is carried out downstream of the crystallization step before recovery of the BPA.

The invention process offers a number of advantages. BPA prepared by the process has improved purity and yield, as thermal cracking of the product is minimized. The adsorbent can be readily regenerated, and the invention process provides a conveniently recyclable system without significant risk of contamination of the acidic ion exchange resin catalyst. The inorganic oxide adsorbent can be substantially regenerated by washing with water to recover better than about 40 percent of the initial adsorption capacity. This is advantageous particularly in a recycled system where the mother liquor is recycled to the reactor. For desorption of acid, water may contain minor amounts of other organics. Preferably, the water injected is greater than 75% water. The absorbent bed can be subsequently dried by phenol purge.

The following examples demonstrate the acid removal step in a bisphenol production according to the invention process.

EXAMPLES 1-5

Various concentrations of phenol sulfonic acids (PSA) in 0.1-1% $H_2O$/phenol were injected through a glass chromatography column filled with 14×28 mesh F1 activated alumina adsorbent from Alcoa as a guard bed. Effluent was collected in discrete samples at timed intervals, from which flow rates could be computed. Samples were titrated for acidity via potentiometric titration to generate effluent acid concentration histories. Titrations using 0.1N or 0.1N KOH titrants were conducted on effluent samples to determine acid breakthrough which is when the amount of acid in the effluent increases from zero to 10 percent of the injected concentration. Following the acid adsorption cycle, the alumina guard bed was regenerated with ten bed weights of water at a WHSV of 4 and at 25° C. The wet bed was dried with four bed weights of phenol at 80° C. Operating conditions and breakthrough responses are given in Table 1. Runs 1 to 2 and 3 to 4 demonstrate the effectiveness of alumina in acid adsorption between the tested temperature range of 80 to 115° C. and regenerability of the alumina substrate. Run 5 demonstrates the effect of space velocity, which limits the adsorption process by finite rates of mass transfer.

overnight with 1 part dry resin and titration of supernatant with 0.100N HCl to determine uptake of base.

Run 6 demonstrates the long-term effectiveness of the alumina adsorbent after the initial acid adsorption and regeneration cycle. Run 7 demonstrates the regeneration and the deleterious effect of increased space velocity under the run 7 test conditions on the adsorber performance. Table 3 demonstrates the absence of poisoning of a small catalyst bed downstream from the alumina bed. At a typical WHSV of 1.0, the 2414 bed weights of alumina-bed effluent passed over the catalyst would correspond to approximately 100 days of operation of a catalyst bed. No significant loss in acid capacity as a result of poisoning by the alumina adsorbent was observed.

TABLE 1

| | | PSA ADSORPTION COLUMN TESTS 25-mm I.D. Column | | | | | |
|---|---|---|---|---|---|---|---|
| Run # | Adsorbent | Temp (°C.) | WHSV | Injected Acidity (ppm PSA) | Bed Length (in) | Bed Weight (g) | Breakthrough Capacity (meq/g) |
| 1 | Fresh alumina | 80 | 2.8 | 6387 | 17.0 | 200.0 | 0.26 |
| 2 | Regen. alumina | 80 | 1.9 | 6281 | 17.0 | 200.0 | 0.21 |
| 3 | Fresh alumina | 114–15 | 1.2 | 2262 | 12.5 | 148.7 | 0.51 |
| 4 | Regen. alumina | 114–15 | 0.8 | 6890 | 12.5 | 148.7 | 0.54 |
| 5 | Regen. alumina | 114–15 | 7.1 | 7078 | 12.5 | 148.7 | 0.18 |

TABLE 2

| | GUARD BED OPERATING CONDITIONS | | | |
|---|---|---|---|---|
| Run # | Injected PSA (ppm) | WHSV | Measured BT (hours) | Measured BT Capacity (meq/g) |
| 6 | 32 | 4.0 | 336 | 0.24 |
| 7 | 349 | 31.0 | 1.3 | 0.14 |

BT = acid breakthrough

TABLE 3

| RESIN BACKTITRATION OF ACID CAPACITY | |
|---|---|
| Sample | Acid Capacity (meq/g) |
| Fresh M-31 | 5.15 |
| Front ½ M-31 Microbed | 5.04 |
| Rear ½ M-31 Microbed | 5.03 |
| Control* | 5.08 |
| Time on line: | 1.6 days |
| Bed Weights Flow: | 2414 (g phenol/g M-31 in microbed) |
| Alumina/M-31: | 14 |
| Temperature (°C.): | 80 |

*Heated 80° C. in fresh phenol for 1.6 days.

EXAMPLES 6–7

Two one-gallon feed vessels were coupled in parallel to serve as a reservoir for phenol fed to an M-31 sulfonic acid ion exchange resin catalyst column and 28×48 mesh F1 alumina guard bed. The alumina bed was pretreated with 0.1N phenol sulfonic acid (PSA) in water until breakthrough at this concentration, to saturate the capacity for PSA adsorption from water which provided an initial condition corresponding to a regenerated guard bed. The bed was then washed with 30 bed weights of deionized water and dried with 4 bed weights of phenol. Flow was driven by nitrogen pressure on the feed vessels, with regulation by a needle valve on the system outlet. The catalyst column contained 132 grams of M-31 and was operated at 85° C. The alumina guard bed was operated at 90° C. and at a WHSV of 4. For the last two days of run number 6, a microbed containing 4.3 (dry) grams of M-31 was placed downstream from the alumina bed to test for the catalyst poisoning.

Feed pots were recharged daily with phenol effluent, such that recycle operation was simulated. Flow rates were determined via timing collection of discrete fractions. Samples of catalyst-bed and alumina-bed effluents were collected three to four times each day, for titration of acidity. After breakthrough of acid in run 6, the bed was regenerated with water. A portion of the alumina was then removed from the bed, and the catalyst bed was bypassed. PSA was doped in the phenol feed at 349 ppm, and fed to the bed at a WHSV of 31. No acid appeared in the effluent until 0.14 milliequivalents/gram adsorption by the alumina bed. Operating conditions and breakthrough responses are given in Table 2. The results of the flow test of the catalyst microbed poisoning test are given in Table 3. Acid capacity was determined by equilibration of 100 parts 0.100N NaOH

EXAMPLE 8

Figure 1:
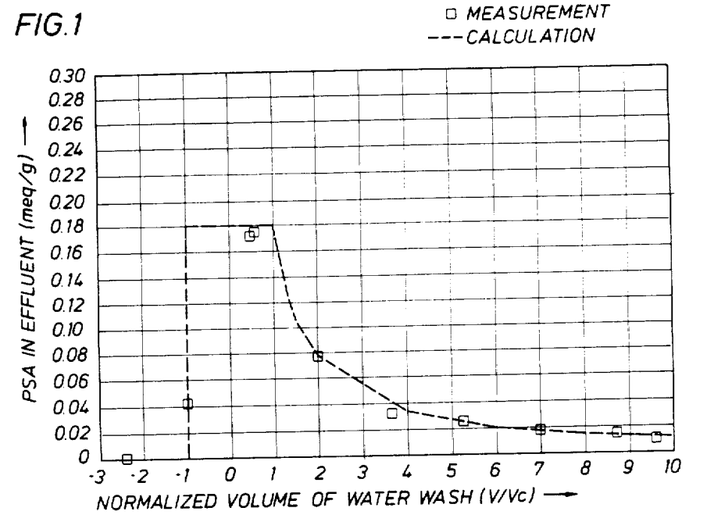
FIGS. 1 and 2 are graphs of effluent or supernatant acidities for the continuous flow experiment of Example 8 and batch experiment of Example 9, respectively.

A continuous flow desorption experiment is described. Following breakthrough of acid in the alumina bed effluent described in Example 6, phenol feed was drained to the top of the alumina bed, and water was added at 25° C. and at WHSV of 4. Water regeneration was continued for 10 bed weights, followed by drying of the bed with 6 bed weights of phenol at WHSV of 4, and at 80° C. Samples of guard bed effluents were collected for titration of desorbed acidity. The results are shown in FIG. 1 where PSA in the effluent in meq/g-fluid is plotted against the volume of water wash normalized by void volume of the bed (V/Vc). Acid desorbed from the bed exceeded the injected concentration (32-ppm PSA) by a factor of nearly 1000. This response demonstrates the efficiency of water regeneration.

EXAMPLE 9

A batch soak-and-drain regeneration experiment is described. Approximately 300 grams of activated alumina was contacted with PSA/phenol in proportions which gave a final PSA concentration of 28 ppm after three days of batch equilibration. The alumina and PSA/phenol supernatant was then charged to a 3-inch diameter glass pipe fitted with a bottom flange equipped with a lower drain valve. Excess PSA was removed by first draining the PSA/phenol supernatant from the bed under gravity, and then by adding fresh phenol upflow to the vessel and draining twice.

Figure 2:
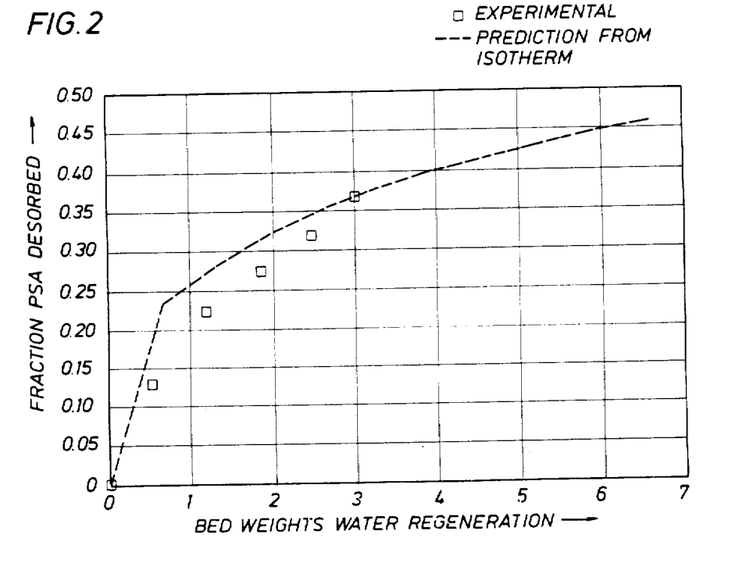

Subsequently, water was added upflow until the top of the bed was covered. After equilibrating overnight, water was drained from the bed with titration of the effluent to determine acidity. The cycle was repeated every 24-hour period. Resulting desorption of acid is shown in FIG. 2. Approximately 40% of the total adsorbed acid (PSA) was desorbed after 5 batch cycles which utilized 3–4 bed weights of water. Batch regeneration may be preferred over a continuous flow regeneration, if water supply is limited to a low linear velocity, such as less than about 5 ft/hr.

EXAMPLES 10–11

Figure 3:
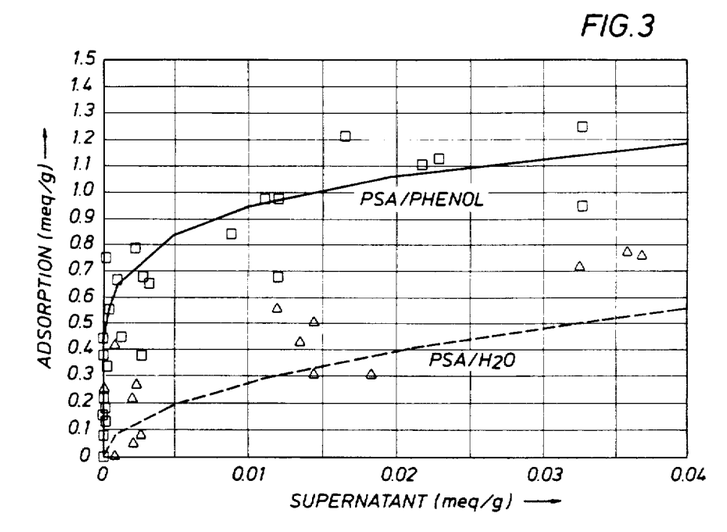
FIGS. 3 and 4 are isotherms for adsorption of phenol sulfonic acid on alumina and silica, respectively.

Isothezms were determined with batch experiments entailing adsorption of PSA from water and from phenol supernatants on F1 activated alumina prewashed with water. A separate isotherm for PSA adsorption from water was obtained by fitting an equilibrium chromatographic model for the Freundlich isotherm to the effluent concentration history of Example 8. Batch adsorption studies were conducted in 50-cc Erlenmeyer flasks at a 15:1 or 30:1 supernatant/solids ratios. Varying concentrations of PSA in water or 1000-ppm $H_2O$/phenol were added to the flasks, and allowed to equilibrate for 3 days. Adsorptions from phenol were conducted at 90° C. while water adsorptions were conducted at 25° C. The results are shown in FIG. 3, along with best fit isotherms. In FIG. 3, adsorption is plotted in meq/g-solid against supernatant in meq/g-fluid.

The concave downward curvature observed in FIG. 3, sometimes called "Langmuir-like" behavior, is that of a favorable isotherm. If a solute (e.g. acid) is fed into a column containing an adsorbent which exhibits a favorable isotherm for this solute, no solute will appear in the effluent of the column until such time as a substantial adsorption capacity of the adsorbent has been satisfied. Since the isotherm for PSA abstraction from phenol lies above the isotherm for abstraction by water in FIG. 3, acid uptake in phenol is greater at a given supernatant concentration. It is therefore possible to adsorb acid from phenol, desorb a portion of this acid via water regeneration, and then adsorb acid again from phenol in a subsequent cycle. Operation can be thus cycled between the phenol and water isotherms, with the amount of acid desorbed by water washing corresponding to the capacity for readsorption of acid in a subsequent adsorption cycle in phenol. The adsorbent can be repeatedly cycled in this manner.

EXAMPLE 12

Figure 4:
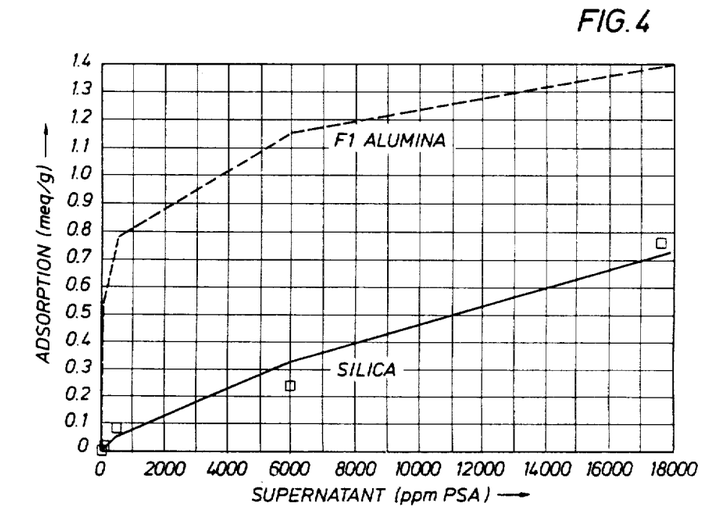
Figure 5:
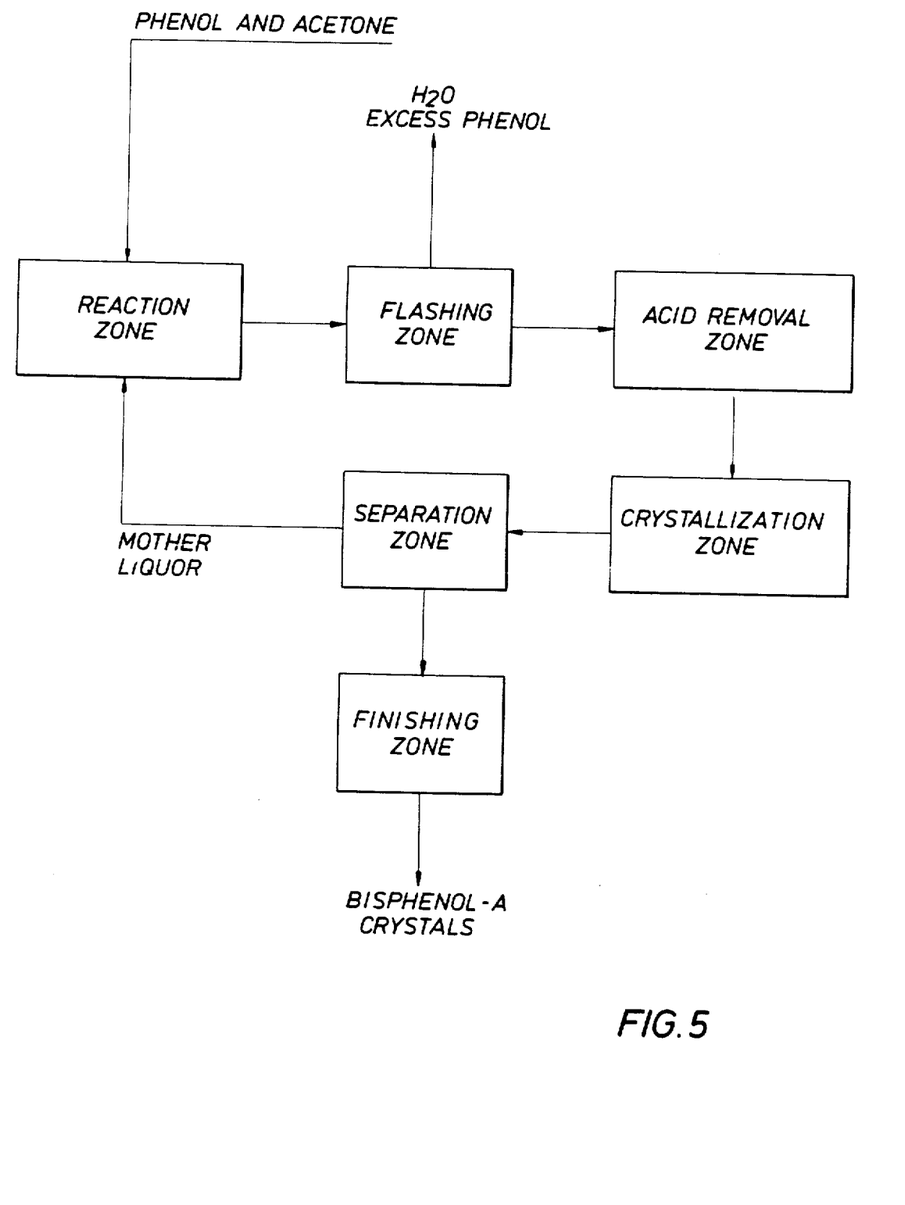
FIG. 5 is a schematic flow diagram illustrating the most preferred embodiment of the invention process.

Isotherms for adsorption of phenol sulfonic acid (PSA) from phenol containing one percent water on silica (Davisil, 30×60 mesh) at 80° C. were determined in batch experiments conducted at a 40:1 supernatant/solids ratio. Varying quantities of PSA were added to the flasks. Supernatants were titrated for acidity after three days of equilibration. A comparison of the resulting isotherm with the best fit-response for alumina is given in FIG. 4. The isotherm for adsorption by silica is nearly linear, and lies beneath the curved, favorable isotherm for alumina. This study indicates alumina is preferred as an adsorbent for PSA in excess phenol.

Flow studies were conducted on a short (7.9 gram) bed of silica in the flow system described above. PSA at 61 ppm was injected into the phenol feed, and passed over the silica bed at WHSV of 293. Acid breakthrough occurred in 30 bed weights of effluent, for an acid capacity of 0.02 meq/g. Water regeneration was attempted with 34 bed weights of demineralized water. After drying with phenol, a second adsorption experiment was conducted at 59 ppm PSA and at WHSV of 244. Acid breakthrough was immediate, which indicated a lack of regenerability via water washing.

Alumina behaves as a weak base (anion) exchanger under process conditions; thus it is an effective acid adsorbent. Silica, with an isoelectric point (pI) of about 2, is an example of a weak acid (cation) exchanger in excess phenol (typically effective pH of about 5–6). Therefore, strong adsorption of acid and water regenerability of silica are not expected.

We claim:

1. A process for the production of a bisphenol comprising the steps of:
   (a) reacting a carbonyl compound selected from the group consisting of ketones and a aldehydes with a stoichiometric excess of a phenolic compound in the presence of an effective amount of an acid ion exchange resin catalyst to produce a reaction product mixture comprising a bisphenol;
   (b) contacting the reaction product mixture containing the bisphenol with an inorganic oxide adsorbent selected from the group consisting of alumina, zirconium oxide, titanium oxide and tin oxide under conditions effective to reduce the acidity of the reaction product mixture; and
   (c) recovering bisphenol from the thus treated reaction product mixture.

2. The process of claim 1 wherein the inorganic oxide adsorbent is activated alumina.

3. The process of claim 1 wherein the carbonyl compound is a ketone.

4. The process of claim 3 wherein the ketone is acetone.

5. The process of claim 1 further comprising the step of
   (d) removing acid from the adsorbent by contact thereof with water.

6. The process of claim 5 wherein the inorganic adsorbent is alumina.

7. A process for the production of a bisphenol comprising the steps of:
   (a) reacting a ketone or an aldehyde with a stoichiometric excess of a phenolic compound in the presence of an effective amount of an acid ion exchange resin catalyst to produce a reaction product solution comprising a bisphenol;
   (b) contacting the reaction product solution containing the bisphenol with an amphoteric oxide substrate having an isoelectric point above the pH of the solution under conditions effective to reduce the acidity of the reaction product solution; and
   (c) recovering bisphenol from the thus treated reaction product solution.

8. The process of claim 6 wherein the amphoteric oxide substrate is selected from the group consisting of alumina, zirconium oxide, titanium oxide and tin oxide.

9. The process of claim 8 wherein the amphoteric oxide substrate is activated alumina.

10. The process of claim 7 further comprising the step of (d) removing acid from the amphoteric oxide substrate by contact thereof with water.

11. The process of claim 10 wherein the amphoteric oxide substrate has an isoelectric point above the pH of the solution.

12. The process of claim 10 wherein the amphoteric oxide substrate is alumina.

13. A process for the production of bisphenol-A comprising the steps of:
   (a) contacting acetone with a stoichiomeric excess of phenol in the presence of an effective amount of an acid ion exchange resin catalyst to produce a reaction product mixture comprising bisphenol-A;
   (b) contacting the reaction product mixture containing bisphenol-A with activated alumina under conditions effective to reduce the acidity of the reaction product mixture; and
   (c) recovering bisphenol-A from the thus treated reaction product mixture.

* * * * *

UNITED STATES PATENT AND TRADEMARK OFFICE
CERTIFICATE OF CORRECTION

PATENT NO. : 5,008,470

DATED : April 16, 1991

INVENTOR(S) : J.B. Powell, et al

It is certified that error appears in the above-identified patent and that said Letters Patent is hereby corrected as shown below:

The title page should be deleted and substitute therefor the attached title page.

Drawing sheets, consisting of Figs. 1-5, as shown on the attached pages, should be added.

Col. 9, line 1 (claim 8, line 1) delete "6" and substitute --7--.

Signed and Sealed this

Twenty-second Day of December, 1992

Attest:

DOUGLAS B. COMER

Attesting Officer

Acting Commissioner of Patents and Trademarks

United States Patent [19]

Powell et al.

[11] Patent Number: 5,008,470
[45] Date of Patent: Apr. 16, 1991

[54] PROCESS FOR PREPARING A BISPHENOL

[75] Inventors: Joseph B. Powell; Christopher W. Uzelmeier, both of Houston, Tex.

[73] Assignee: Shell Oil Company, Houston, Tex.

[21] Appl. No.: 444,580

[22] Filed: Nov. 30, 1989

[51] Int. Cl.$^5$ .................. C07C 37/20; C07C 39/16
[52] U.S. Cl. .................. 568/727; 568/724; 568/728
[58] Field of Search ............ 568/722, 724, 727, 728
[56] References Cited

U.S. PATENT DOCUMENTS

| | | | |
|---|---|---|---|
| 4,160,110 | 7/1979 | Carnahan, Jr. | 568/703 |
| 4,169,211 | 9/1979 | Ligorati et al. | 568/724 |
| 4,396,728 | 8/1983 | Faler | 521/32 |
| 4,533,764 | 8/1985 | Chang et al. | 568/724 |
| 4,766,254 | 8/1988 | Faler et al. | 568/724 |
| 4,876,395 | 10/1989 | Kissinger | 568/728 |

FOREIGN PATENT DOCUMENTS

5821633 7/1981 Japan .................. 568/727
58021633 2/1983 Japan .

Primary Examiner—Werren B. Lone

[57] ABSTRACT

The present disclosure is directed to acid scavenging in the acid-catalyzed preparation of a bisphenol by condensation of a phenolic compound and a carbonyl compound. During the preparation, strong acids leach from the acidic ion exchange resin catalyst into the reaction effluent. These acids can be scavenged effectively and without contamination by an inorganic oxide before purification of the product. The acid scavenging improves the product quality and yield by reducing acid catalyzed cracking of bisphenols during purification and finishing steps.

13 Claims, 3 Drawing Sheets